(12) United States Patent
Sathaye et al.

(10) Patent No.: US 12,254,960 B2
(45) Date of Patent: Mar. 18, 2025

(54) QUANTUM COMPUTING TECHNIQUES FOR DETERMINING GENE PREDICTORS IN GENE REGULATORY NETWORKS

(71) Applicant: Optum Services (Ireland) Limited, Dublin (IE)

(72) Inventors: Ninad D. Sathaye, Bangalore (IN); Paul J. Godden, London (GB); Vicente Ruben Del Pino Ruiz, Dublin (IE); Matthew R. Versaggi, Plymouth, MN (US)

(73) Assignee: Optum Services (Ireland) Limited, Dublin (IE)

( * ) Notice: Subject to any disclaimer, the term of this patent is extended or adjusted under 35 U.S.C. 154(b) by 483 days.

(21) Appl. No.: 17/645,130

(22) Filed: Dec. 20, 2021

(65) Prior Publication Data

US 2023/0197193 A1    Jun. 22, 2023

(51) Int. Cl.
*G16B 25/10* (2019.01)
*G06N 10/20* (2022.01)
*G06N 10/60* (2022.01)
*G16H 50/20* (2018.01)

(52) U.S. Cl.
CPC ............ *G16B 25/10* (2019.02); *G06N 10/20* (2022.01); *G06N 10/60* (2022.01); *G16H 50/20* (2018.01)

(58) Field of Classification Search
CPC ........ G16B 25/10; G06N 10/20; G06N 10/60; G16H 50/20
See application file for complete search history.

(56) References Cited

U.S. PATENT DOCUMENTS

| | | | |
|---|---|---|---|
| 8,301,387 B2 | 10/2012 | Hwa et al. | |
| 2008/0140749 A1* | 6/2008 | Amato | G06N 10/00 708/490 |
| 2019/0095561 A1* | 3/2019 | Pednault | G06F 17/16 |
| 2019/0244680 A1 | 8/2019 | Rolfe et al. | |

(Continued)

FOREIGN PATENT DOCUMENTS

| | | |
|---|---|---|
| CN | 110210529 A | 9/2019 |
| CN | 110473591 A | 11/2019 |
| WO | 2021/087646 A1 | 5/2021 |

OTHER PUBLICATIONS

Shah et al. "Entangling unitary gates on distant qubits with ancilla feedback," Nov. 14, 2013, SUPA Department Of Physics, University of Strathclyde, Glasgow G4 0NG, UK, pp. 1-8. (Year: 2013).*

(Continued)

*Primary Examiner* — Ricky Go
(74) *Attorney, Agent, or Firm* — Alston & Bird LLP

(57) ABSTRACT

Various embodiments of the present invention provide methods, apparatus, systems, computing devices, computing entities, and/or the like for performing health-related predictive data analysis. Certain embodiments of the present invention utilize systems, methods, and computer program products that perform health-related predictive data analysis by generating an optimal predictor set for a gene regulatory network using a quantum logic circuit that comprises one or more quantum logic subcircuits for each quantum processing unit that is associated with a quantum subcircuit and is configured to perform a conjunctive phase logic operation performed on each ancilla bit of a quantum subcircuit.

20 Claims, 12 Drawing Sheets

(56) References Cited

U.S. PATENT DOCUMENTS

| | | | |
|---|---|---|---|
| 2020/0356890 A1 | 11/2020 | Ashrafi | |
| 2021/0287761 A1 | 9/2021 | Underwood et al. | |
| 2022/0398460 A1* | 12/2022 | Dalli | G06F 18/2163 |

OTHER PUBLICATIONS

"Gene Expression Omnibus," NCBI, (1 page), (Online), [Retrieved from the Internet Apr. 9, 2022] <URL: https://www.ncbi.nlm.nih.gov/geo/>.

"KEGG—Kyoto Encyclopedia of Genes and Genomes," Kanehisa Laboratories, (1 page), (Year: 1995), (Online), [Retrieved from the Internet Apr. 9, 2022] <URL: https://www.genome.jp/kegg/>.

"Quantum Machine Shows Promise For Biological Research," Science Daily, Feb. 27, 2018, University of Southern California, (3 pages), [Retrieved from the Internet Sep. 16, 2021] <URL: https://www.sciencedaily.com/releases/2018/02/180227142116.htm>.

"The Encode Project," Encode, Stanford University, (Year: 2022), (5 pages), (online) [Retrieved from the Internet Apr. 9, 2022] <URL: https://www.encodeproject.org/>.

Balu, Radhakrishnan et al. "Bayesian Networks Based Hybrid Quantum-Classical Machine Learning Approach To Elucidate Gene Regulatory Pathways," arXiv Preprint arXiv:1901.10557v1 [cs.LG], Jan. 23, 2019, (9 pages).

Corblin, Fabien et al. "A SAT-Based Approach To Decipher Gene Regulatory Networks," Integrative Post-Genomics, (Year: 2007), (9 pages), RIAMS, Lyon.

Epstein, Douglas J. "Cis-Regulatory Mutations In Human Disease," Briefings In Functional Genomics and Proteomics, vol. 8, No. 4, Jul. 29, 2009, pp. 310-316, DOI: 10.1093/bfgp/elp021, PMID: 19641089.

Gomes, Carla P. et al. "Satisfiability Solvers—Chapter 2," Handbook of Knowledge Representation, vol. 3, (Year 2008), pp. 89-134, Computer Science, DOI:10.1016/S1574-6526(07)03002-7.

Grozinger, Lewis et al. "Pathways To Cellular Supremacy In Biocomputing," Nature Communications, vol. 10, No. 1, Nov. 20, 2019, pp. 1-11, DOI: 10.1038/s41467-019-13232-z.

Guo, Wensheng et al. "A Parallel Attractor Finding Algorithm Based On Boolean Satisfiability For Genetic Regulatory Networks," PLoS|ONE, vol. 9, No. 4:e94258, Apr. 9, 2014, pp. 1-10, DOI: 10.1371/journal.pone.0094258.

Jafari, Mina et al. "A Hybrid Framework For Reverse Engineering Of Robust Gene Regulatory Networks," Artificial Intelligence In Medicine, vol. 79, Jun. 2017, pp. 15-27, DOI: 10.1016/j.artmed.2017.05.004, Epub: Jun. 9, 2017, PMID: 28602483.

Khan, Abhinandan et al. "Construction of Gene Regulatory Networks Using Recurrent Neural Networks and Swarm Intelligence," Hindawa Publicating Corporation, Scientifica, vol. 26, Article ID 1060843, (14 pages), DOI: 10.1155/2016/1060843.

Lin, Pey-Chang Kent et al. "Inference of Gene Predictor Set Using Boolean Satisfiability," arXiv Preprint arXiv:1005.4812v1 [q-bio.GN], May 26, 2010, (9 pages), DOI: 10.48550/arXiv.1005.4812.

Noonan, James P. et al. "Genomics Of Long-Range Regulatory Elements," Annual Review of Genomics and Human Genetics, vol. 11, Sep. 22, 2010, ePub: May 3, 2010, pp. 1-24, DOI: 10.1146/annurev-genom-082509-141651, PMID: 20438361.

Rottger, Richard et al. "How Little Do We Actually Know? On the Size of Gene Regulatory Networks," IEEE/ACM Transactions On Computational Biology and Bioinformatics / IEEE, ACM, vol. 9, No. 5, May 2012, (4 pages), DOI:10.1109/TCBB.2012.71.

Schlitt, Thomas et al. "Modelling In Molecular Biology: Describing Transcription Regulatory Networks At Different Scales," Philosophical Transactions Of The Roytal Society B, vol. 361, Feb. 1, 2006, pp. 483-494, DOI: 10.1098/rstb.2005.1806.

The FANTOM Consortium and the RIKEN PMI and CLST (DGT). "A Promoter-Level Mammalian Expression Atlas," Nature, vol. 507, No. 7493, Mar. 27, 2014, pp. 462-470, DOI: 10.1038/nature13182, PMID: 24670764, HHS Public Access, Author Manuscript, (40 pages).

Visel, Axel et al. "Genomic Views of Distant-Acting Enhancers," Nature, vol. 461, Sep. 9, 2009, pp. 199-2005, DOI: 10.1038/nature08451.

Wang, Zidong et al. "Dynamics Analysis of Gene Regulatory Networks," International Journal of Systems Science, vol. 41, No. 1, Jan. 8, 2010, pp. 1-4.

* cited by examiner

500

| Data table | | | | |
|---|---|---|---|---|
| ID_REF | VALUE | 5455178010_A.Avg_NBEADS | 5455178010_A.BEAD_STDERR | 5455178010_A.Detection Pval |
| ILMN_1762337 | 111.824 | 24 | 5.172565 | 0.2064935 |
| ILMN_2055271 | 126.907 | 21 | 8.396618 | 0.03896104 |
| ILMN_1736007 | 91.20126 | 17 | 4.822516 | 0.7818182 |
| ILMN_2383229 | 110.3134 | 18 | 7.833842 | 0.238961 |
| ILMN_1806310 | 101.7956 | 14 | 4.944949 | 0.4727273 |
| ILMN_1779670 | 96.83981 | 29 | 5.057463 | 0.6246753 |

FIG. 5

| Time | Gene1 | Gene2 | Gene3 |
|------|-------|-------|-------|
| t1   | 0     | 1     | 0     |
| t2   | 1     | 0     | 0     |

| Time t | | | Time t+1 | | |
|---|---|---|---|---|---|
| G1 | G2 | G3 | G1' | G2' | G3' |
| 0 | 0 | 0 | 0 | 0 | 1 |
| 0 | 0 | 1 | 0 | 0 | 1 |
| 0 | 1 | 0 | 1 | 0 | 1 |
| 0 | 1 | 1 | 1 | 0 | 1 |
| 1 | 0 | 0 | 0 | 0 | 0 |
| 1 | 0 | 1 | 1 | 1 | 0 |
| 1 | 1 | 0 | 0 | 0 | 0 |
| 1 | 1 | 1 | 1 | 1 | 0 |

FIG. 12

QUANTUM COMPUTING TECHNIQUES FOR DETERMINING GENE PREDICTORS IN GENE REGULATORY NETWORKS

BACKGROUND

Various embodiments of the present invention address technical challenges related to performing health-related predictive data analysis. Various embodiments of the present invention address the shortcomings of existing health-related predictive data analysis systems and disclose various techniques for efficiently and reliably performing health-related predictive data analysis.

BRIEF SUMMARY

In general, embodiments of the present invention provide methods, apparatus, systems, computing devices, computing entities, and/or the like for performing health-related predictive data analysis. Certain embodiments of the present invention utilize systems, methods, and computer program products that perform health-related predictive data analysis by generating an optimal predictor set for a gene regulatory network using a quantum logic circuit that comprises one or more quantum logic subcircuits for each quantum processing unit that is associated with a quantum subcircuit and is configured to perform a conjunctive phase logic operation performed on each ancilla bit of a quantum subcircuit.

In accordance with one aspect, a method is provided. In one embodiment, the method comprises: identifying, based at least in part on the gene expression data for the plurality of genes, a plurality of potential predictor sets for the target gene designation, wherein each potential predictor set is associated with one or more cross-temporal gene state transformation relationships; for each potential predictor set: generating a conjunctive predictor set representation that describes a conjunction of one or more transformation relationship models associated with the one or more cross-temporal gene state transformation relationships; for each transformation relationship model, generating a quantum processing unit that comprises: (i) a plurality of gene designation superposition qubits for a plurality of affected qubits of the cross-temporal gene transformation relationship that is associated with the transformation relationship model, and (ii) an ancilla qubit whose value is determined based at least in part on the plurality of gene designation superposition qubits; generating a quantum logic circuit that: (i) comprises one or more quantum logic subcircuits for each quantum processing unit, and (ii) is configured to perform a conjunctive phase logic operation on each ancilla bit; and generating an eligibility indicator for the potential predictor set based at least in part on an output of the conjunctive phase logic operation; determining the optimal predictor set based at least in part on each potential predictor set having an affirmative eligibility indicator; and performing one or more prediction-based actions based at least in part on the optimal predictor set.

In accordance with another aspect, a computer program product is provided. The computer program product may comprise at least one computer-readable storage medium having computer-readable program code portions stored therein, the computer-readable program code portions comprising executable portions configured to: identify, based at least in part on the gene expression data for the plurality of genes, a plurality of potential predictor sets for the target gene designation, wherein each potential predictor set is associated with one or more cross-temporal gene state transformation relationships; for each potential predictor set: generate a conjunctive predictor set representation that describes a conjunction of one or more transformation relationship models associated with the one or more cross-temporal gene state transformation relationships; for each transformation relationship model, generate a quantum processing unit that comprises: (i) a plurality of gene designation superposition qubits for a plurality of affected qubits of the cross-temporal gene transformation relationship that is associated with the transformation relationship model, and (ii) an ancilla qubit whose value is determined based at least in part on the plurality of gene designation superposition qubits; generate a quantum logic circuit that: (i) comprises one or more quantum logic subcircuits for each quantum processing unit, and (ii) is configured to perform a conjunctive phase logic operation on each ancilla bit; and generate an eligibility indicator for the potential predictor set based at least in part on an output of the conjunctive phase logic operation; determine the optimal predictor set based at least in part on each potential predictor set having an affirmative eligibility indicator; and perform one or more prediction-based actions based at least in part on the optimal predictor set.

In accordance with yet another aspect, an apparatus comprising at least one processor and at least one memory including computer program code is provided. In one embodiment, the at least one memory and the computer program code may be configured to, with the processor, cause the apparatus to: identify, based at least in part on the gene expression data for the plurality of genes, a plurality of potential predictor sets for the target gene designation, wherein each potential predictor set is associated with one or more cross-temporal gene state transformation relationships; for each potential predictor set: generate a conjunctive predictor set representation that describes a conjunction of one or more transformation relationship models associated with the one or more cross-temporal gene state transformation relationships; for each transformation relationship model, generate a quantum processing unit that comprises: (i) a plurality of gene designation superposition qubits for a plurality of affected qubits of the cross-temporal gene transformation relationship that is associated with the transformation relationship model, and (ii) an ancilla qubit whose value is determined based at least in part on the plurality of gene designation superposition qubits; generate a quantum logic circuit that: (i) comprises one or more quantum logic subcircuits for each quantum processing unit, and (ii) is configured to perform a conjunctive phase logic operation on each ancilla bit; and generate an eligibility indicator for the potential predictor set based at least in part on an output of the conjunctive phase logic operation; determine the optimal predictor set based at least in part on each potential predictor set having an affirmative eligibility indicator; and perform one or more prediction-based actions based at least in part on the optimal predictor set.

BRIEF DESCRIPTION OF THE DRAWINGS

Figure 1:
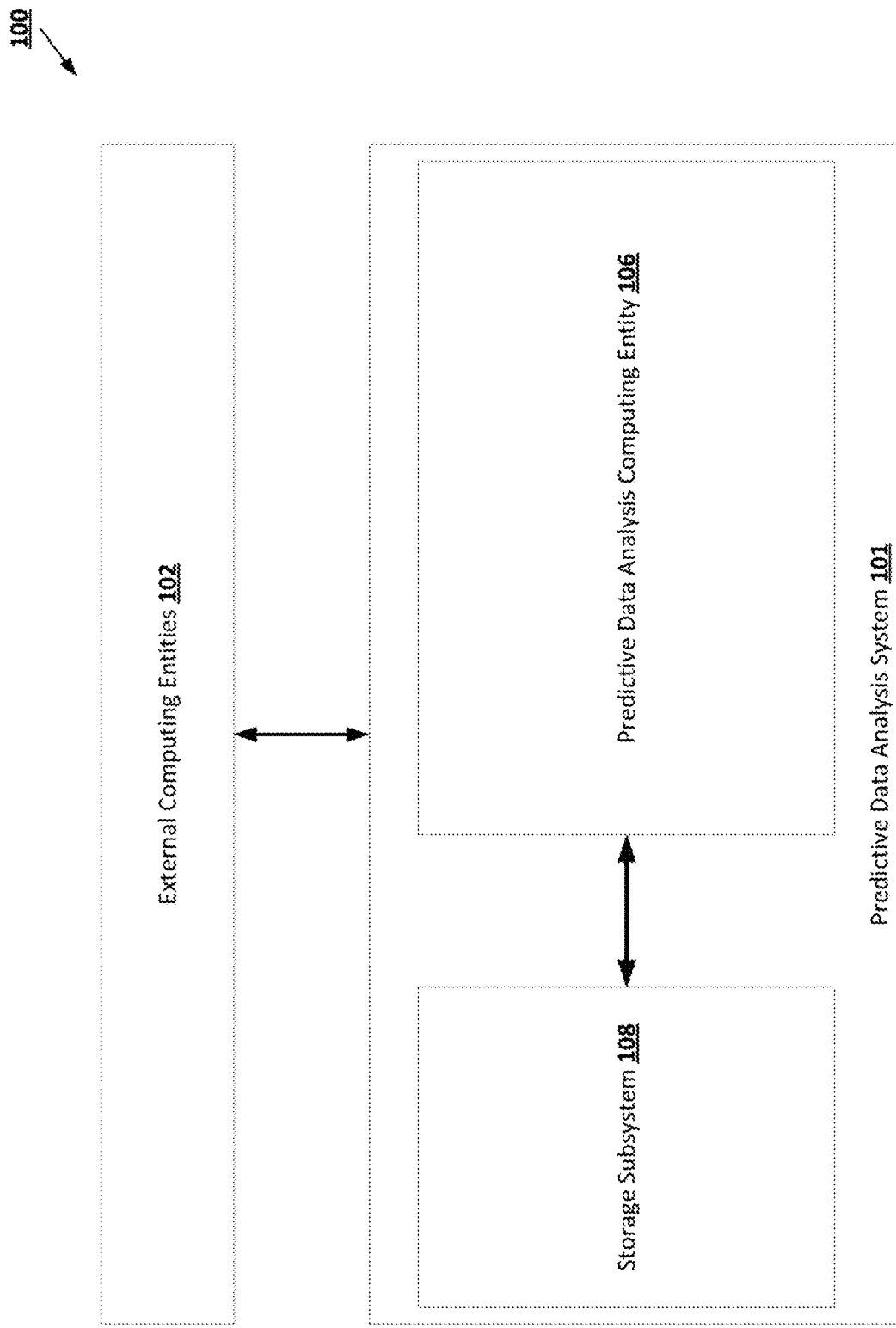

Having thus described the invention in general terms, reference will now be made to the accompanying drawings, which are not necessarily drawn to scale, and wherein:

FIG. 1 provides an exemplary overview of an architecture that can be used to practice embodiments of the present invention.

Figure 2:
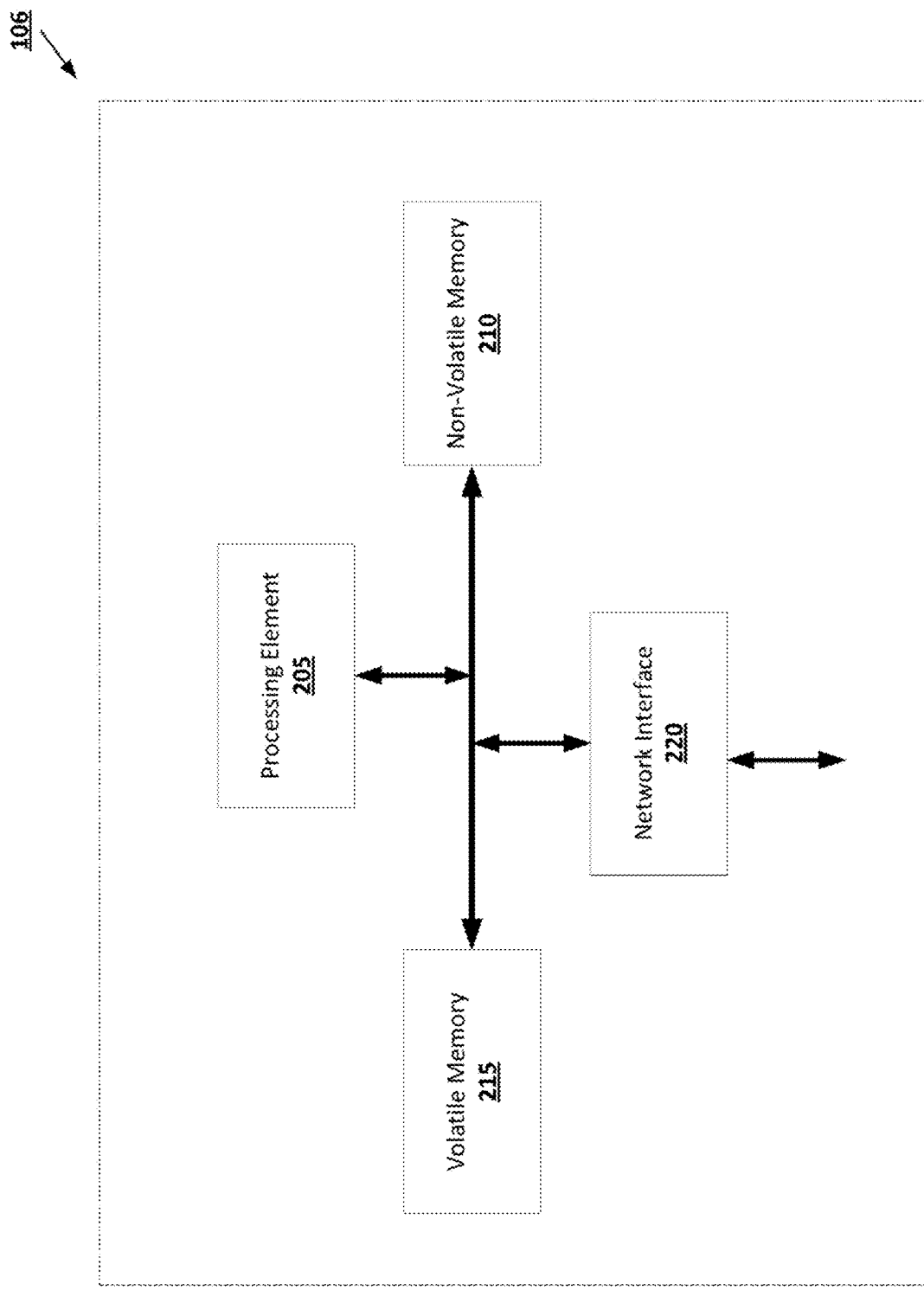

FIG. 2 provides an example predictive data analysis computing entity in accordance with some embodiments discussed herein.

Figure 3:
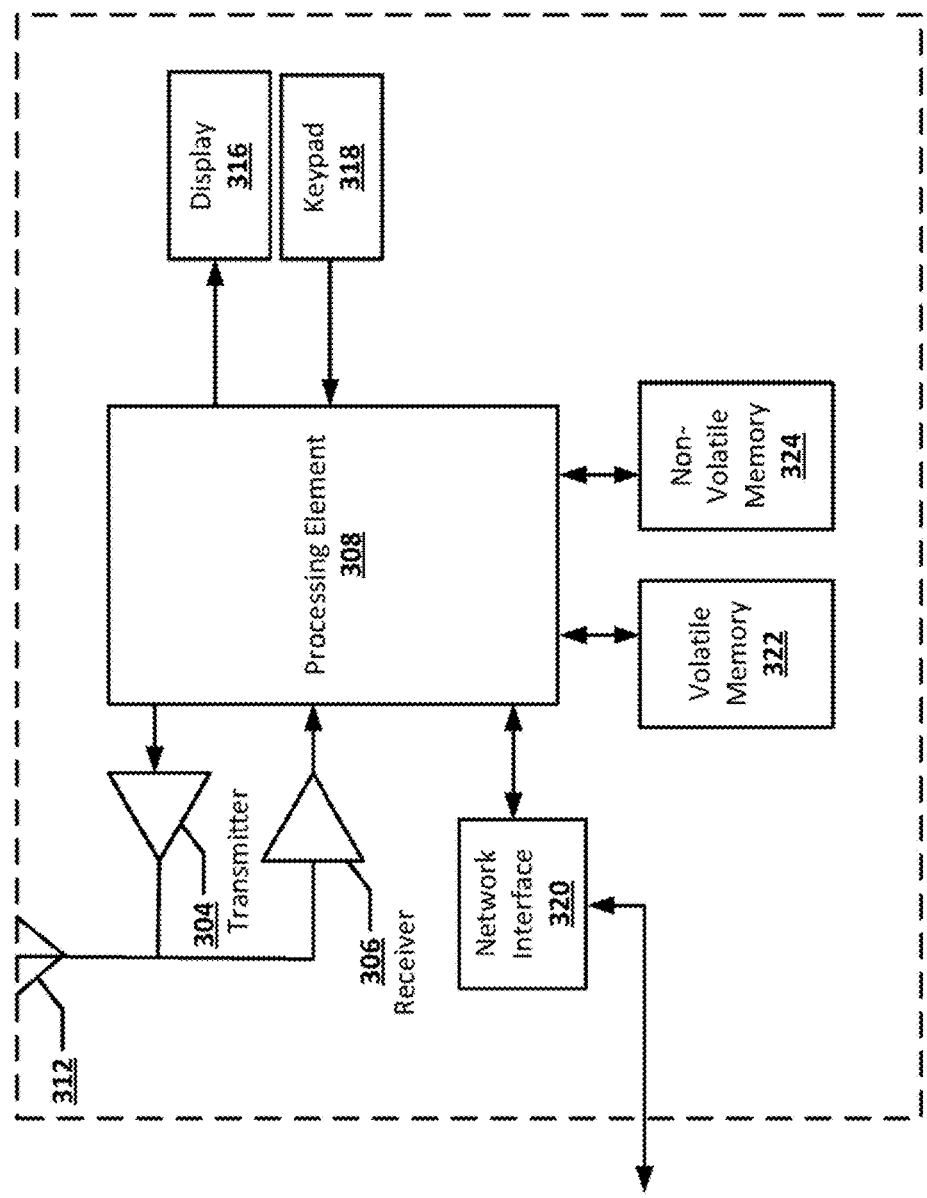

FIG. 3 provides an example external computing entity in accordance with some embodiments discussed herein.

Figure 4:
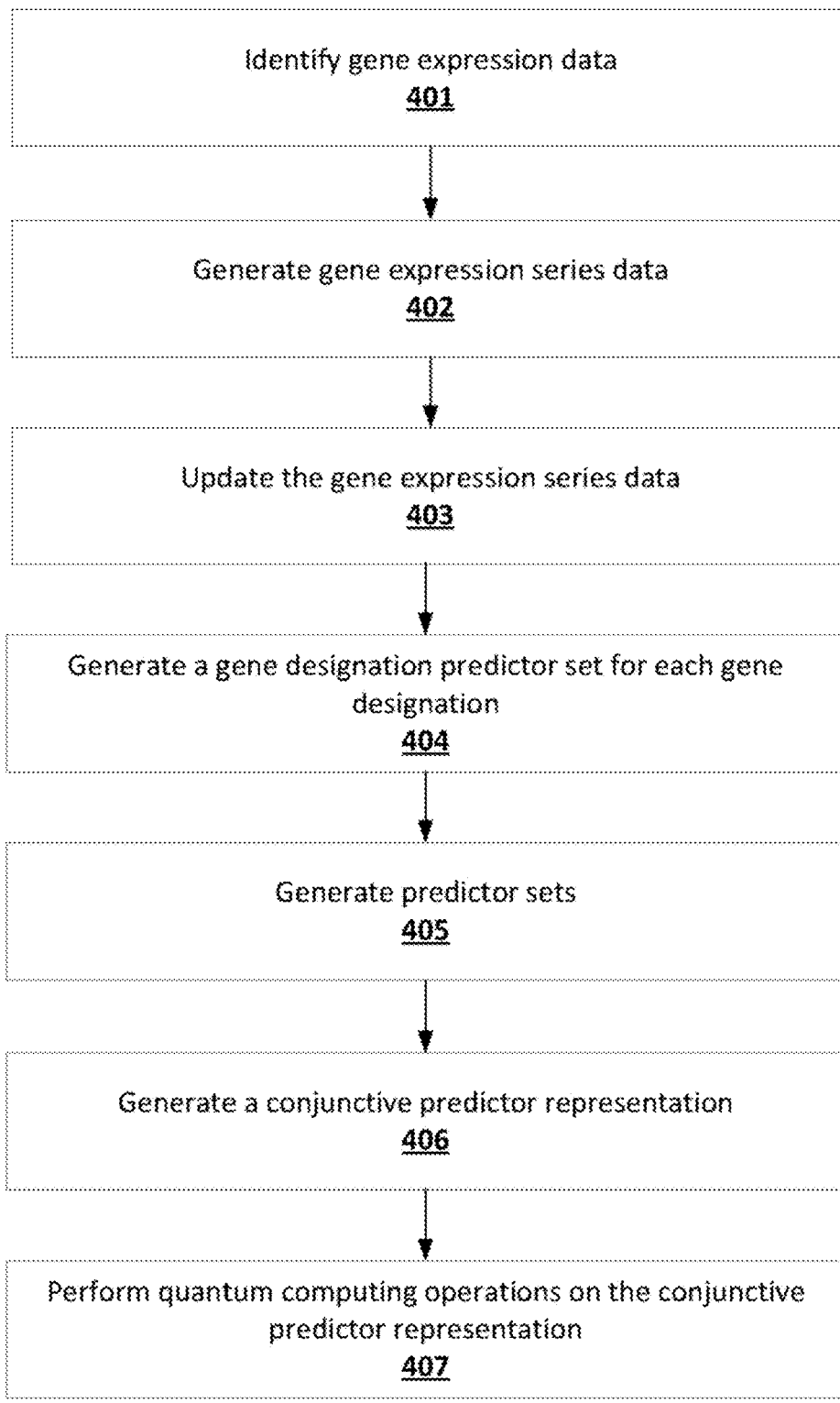

FIG. 4 is a flowchart diagram of an example process for determining an optimal predictor set based at least in part on a particular set of gene expression data in accordance with some embodiments discussed herein.

FIG. 5 provides an operational example of gene expression data in accordance with some embodiments discussed herein.

Figure 6:
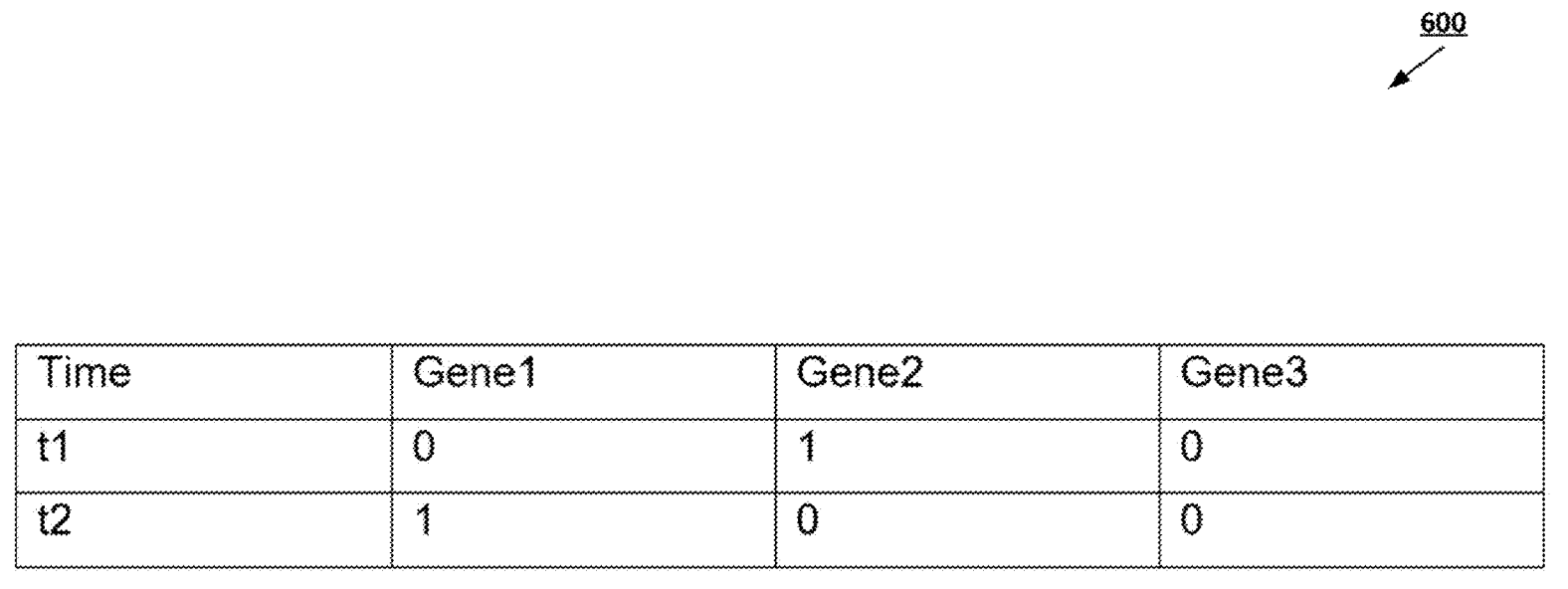

FIG. 6 provides an operational example of gene expression series data in accordance with some embodiments discussed herein.

Figure 7:
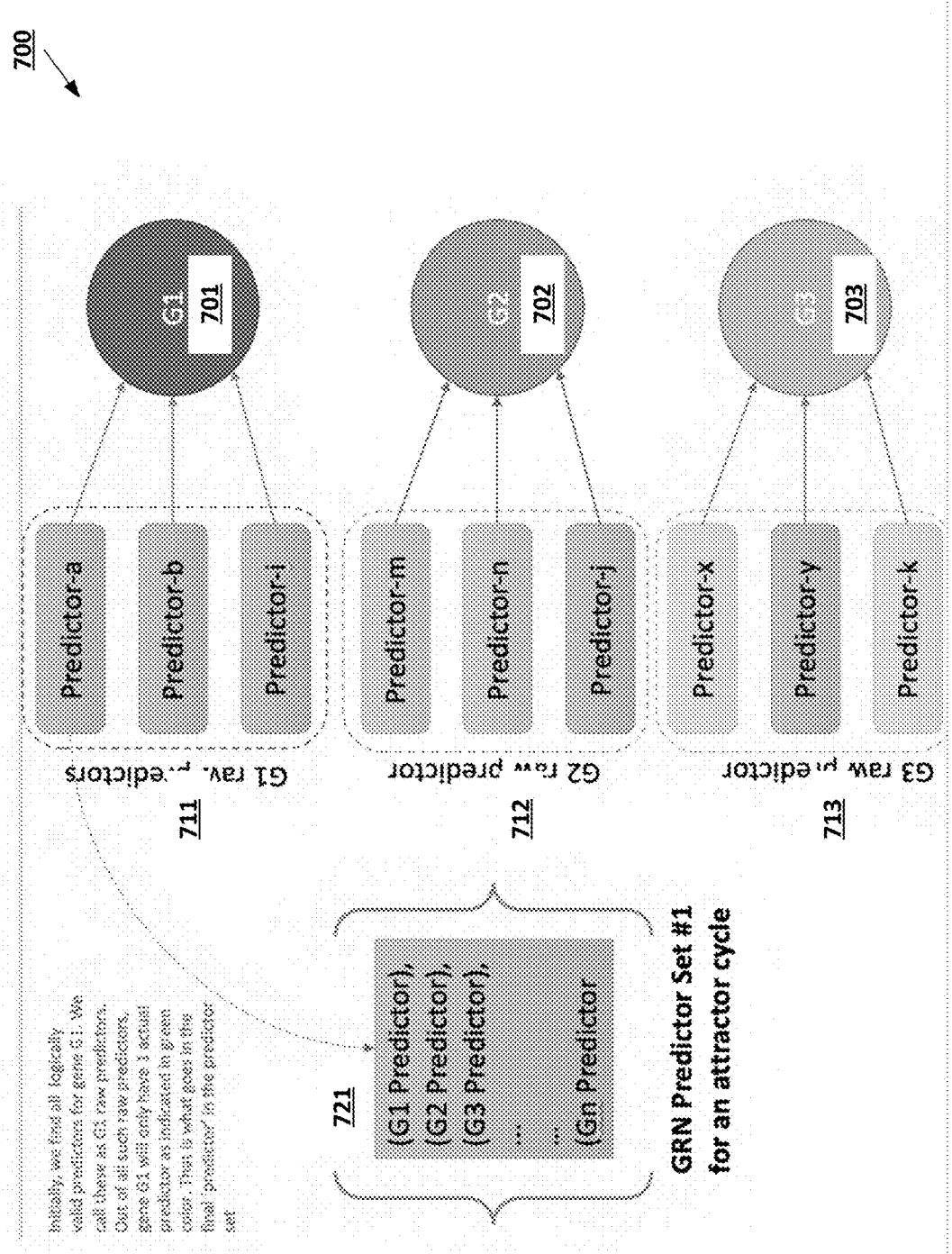

FIG. 7 provides an operational example of generating a potential predictor set in accordance with some embodiments discussed herein.

Figure 8:
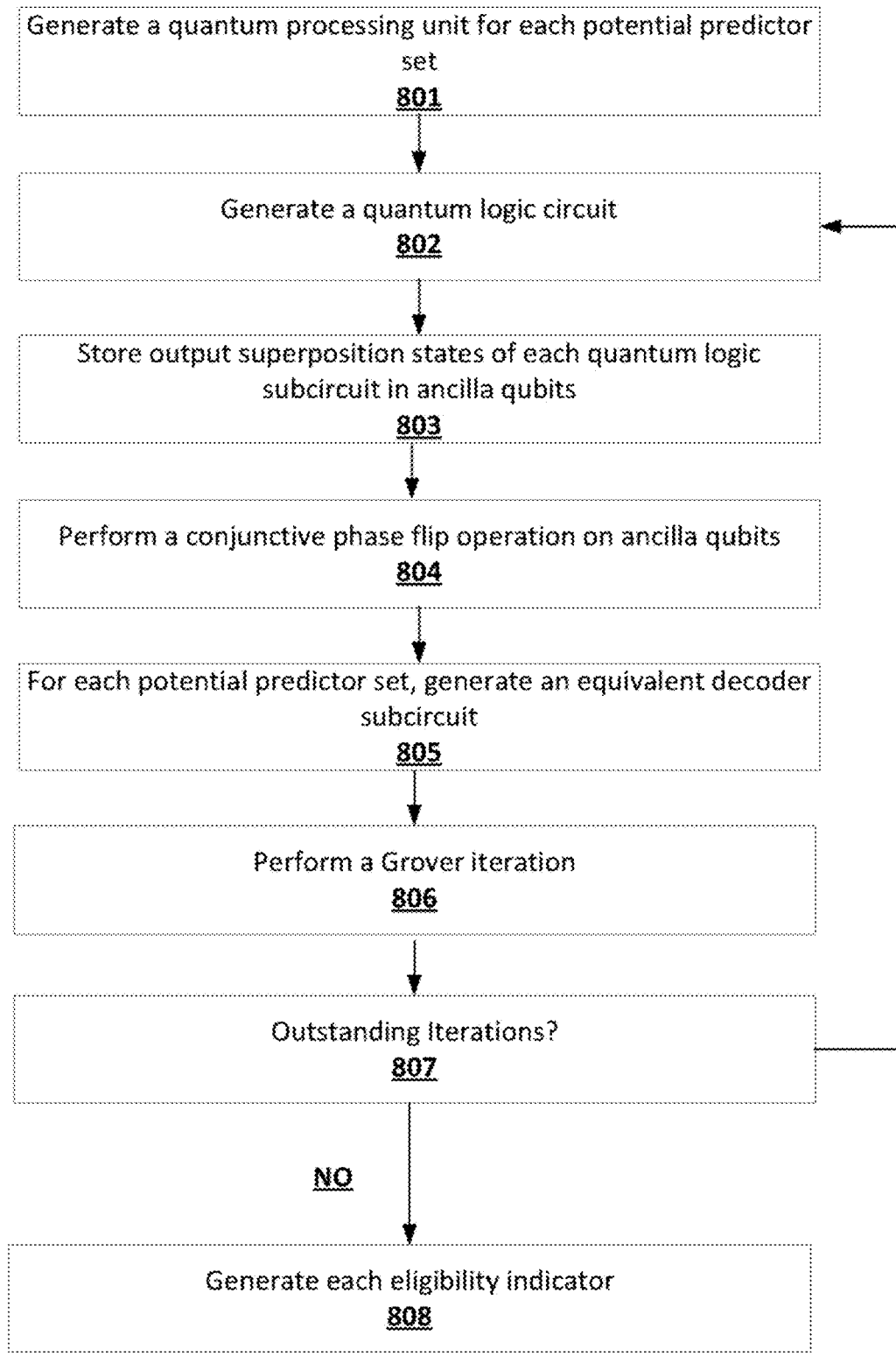

FIG. 8 is a flowchart diagram of an example process for performing computing operations to determine an optimal predictor set for a gene regulatory network based at least in part on a conjunctive predictor representation of state transition data for the gene regulatory network in accordance with some embodiments discussed herein.

Figure 9:
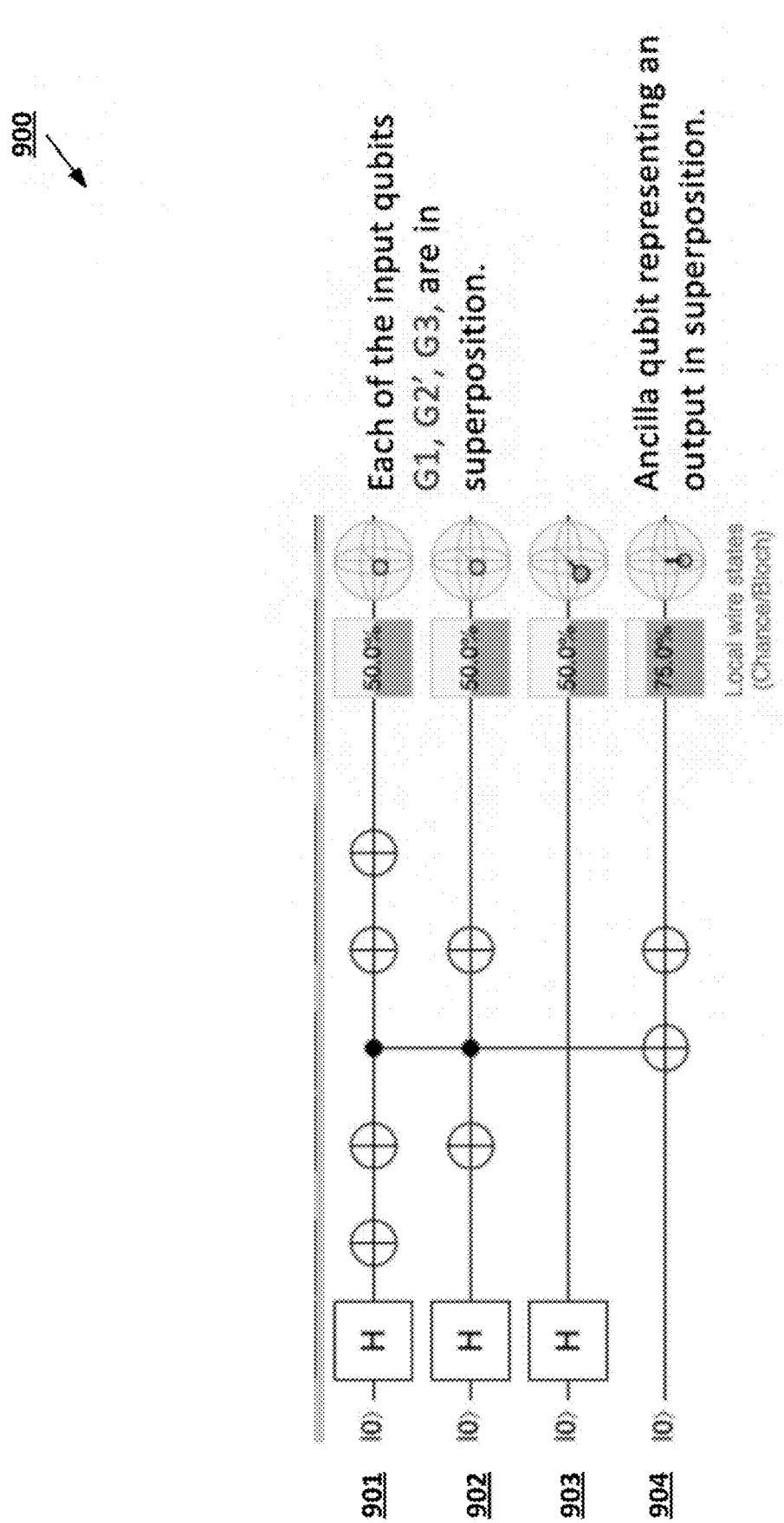

FIG. 9 provides an operational example of a quantum processing unit in accordance with some embodiments discussed herein.

Figure 10:
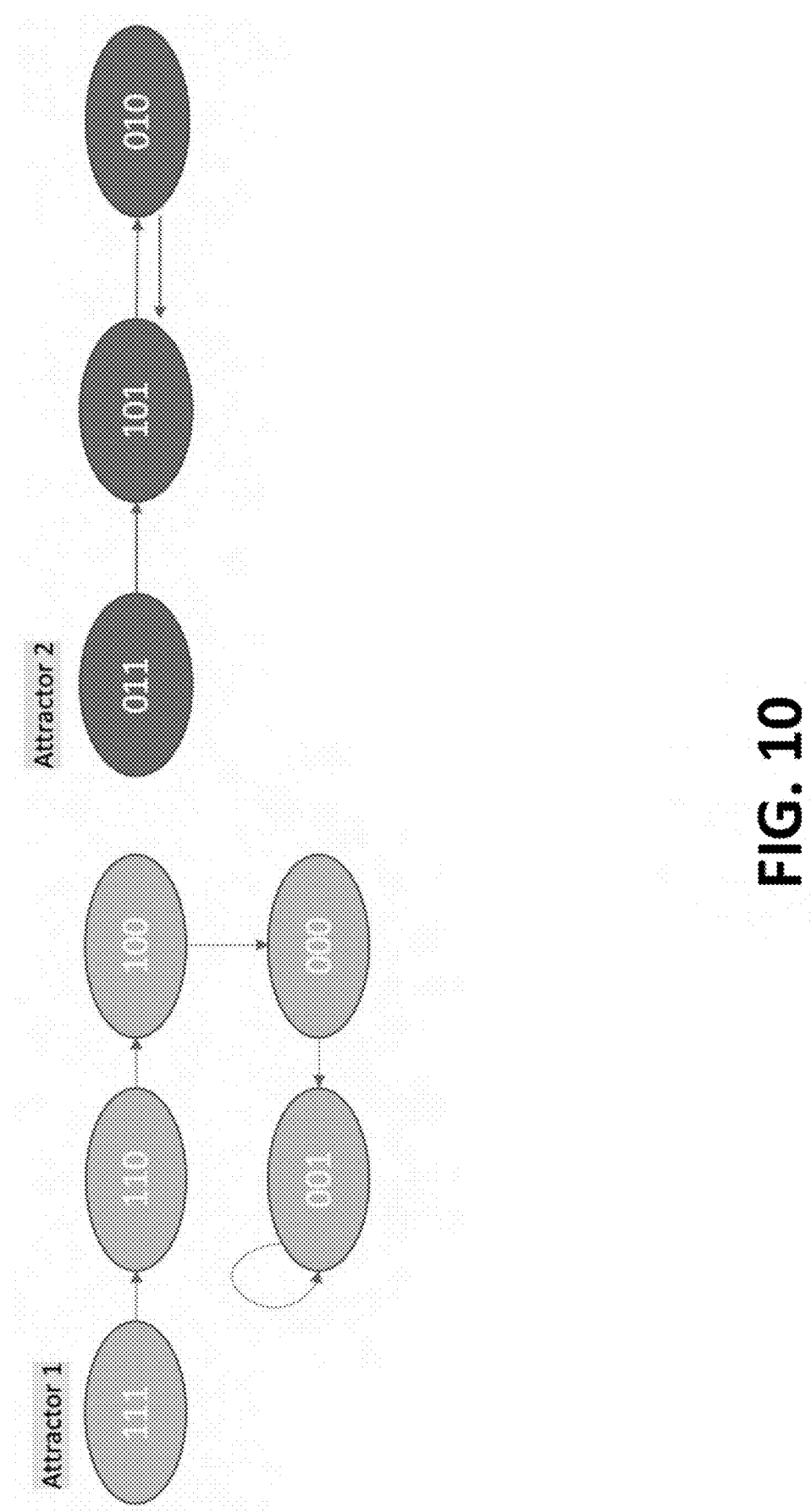

FIG. 10 provides an operational example of two steady/attractor states for a gene regulatory network in accordance with some embodiments discussed herein.

Figure 11:
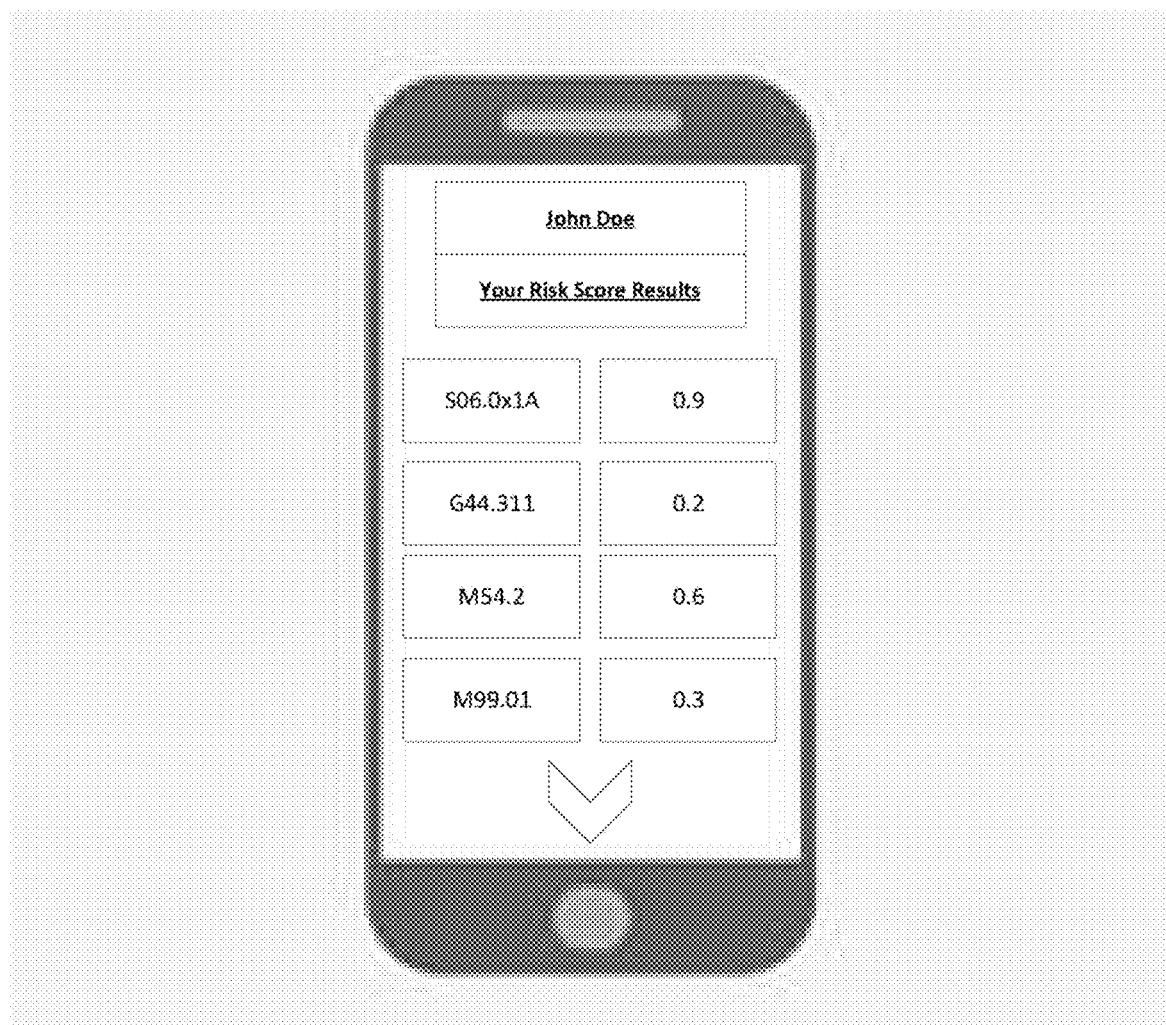

FIG. 11 provides an operational example of a predictive output user interface in accordance with some embodiments discussed herein.

FIG. 12 provides an operational example of gene expression state transition data in accordance with some embodiments discussed herein.

DETAILED DESCRIPTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis.

I. Overview and Technical Advantages

Generating gene regulatory networks from gene expression data in a computationally efficient manner is a major challenge facing the field of computational genetics. See, e.g. Moerman et al., "GRNBoost2 and Arboreto: efficient and Scalable Inference of Gene Regulatory Networks," 35 (12) Bioinformatics 2159-2161 (2019) (available online at https://pubmed.ncbi.nlm.nih.gov/30445495/) ("Inferring a Gene Regulatory Network (GRN) from gene expression data is a computationally expensive task, exacerbated by increasing data sizes due to advances in high-throughput gene profiling technology, such as single-cell RNA-seq.").

Various embodiments of the present invention address the above-noted challenges associated with computational complexity of generating gene regulatory networks from gene expression data by utilizing quantum computing techniques. For example, some embodiments comprise generating an optimal predictor set for a gene regulatory network using a quantum logic circuit that comprises one or more quantum logic subcircuits for each quantum processing unit that is associated with a quantum subcircuit and is configured to perform a conjunctive phase logic operation performed on each ancilla bit of a quantum subcircuit. By using the noted techniques, various embodiments of the present invention address the technical challenges associated with generating gene regulatory networks from gene expression data in a computationally efficient manner and make important contributions to the field of computational genomics.

Moreover, various embodiments of the present invention address technical challenges related to improving computational efficiency and/or operational reliability of performing health-related predictive data analysis. Health-related predictive data analysis systems face substantial challenges because they are tasked with integrating predictive insights related to physiological diversity across the human population (e.g., the genetic diversity of human genome across humans). Because of the noted challenges, various existing predictive data analysis solutions are either highly ineffective and/or too computationally costly. To address the noted concerns related to computational efficiency and/or operational reliability of performing health-related predictive data analysis, various embodiments of the present invention introduce innovative techniques for generating gene regulatory networks in a computationally efficient manner to enable performing health condition modeling in a reliable but efficient manner.

II. Definitions

The term "gene expression data" may refer to a data construct that describes, for each gene of a plurality of observed genes of a monitored individual, a recorded expression value at each of a plurality of timesteps. For example, the gene expression data may describe that a first gene is expressed with a first expression value at time $t_1$, a second expression value at time $t_2$, and so on, while a second gene is expressed with a third expression value at a time $t_3$, a fourth expression value at time $t_4$, and so on. In some embodiments, gene expression data is used to generate gene expression series data. The gene expression series data may describe, for each timestep of a plurality of timesteps, which genes are activated/expressed at the particular timestep via an activation/expression state indicator for each gene at a particular timestep. For example, the gene expression series data may describe that, at a time $t_1$, a first gene is activated/expressed while a second gene is not activated/expressed. In some embodiments, to determine whether a particular gene is activated/expressed at a particular timestep, the expression value for the particular gene and the particular timestep may be extracted from the gene series data. If the expression value for the particular gene and the particular timestep satisfies (e.g., exceeds) a threshold expression value, then the gene expression series data may describe that the particular gene is activated/expressed at the particular timestep.

The term "cross-temporal gene state change frequency indicator" may refer to a data construct that describes a measure of how frequently the activation/expression state indicator of a corresponding gene changes across the various timesteps described by the gene expression series data. For example, the cross-temporal gene state change frequency indicator for a particular gene may be determined based at least in part on at least one of: (i) whether the activation/expression state indicator of the particular gene changes at all during all of the timesteps of the gene expression series data, (ii) whether the activation/expression state indicator of the particular gene changes at least once during each defined-size timestep window of the gene expression series data, (iii) how often the activation/expression state indicator of the particular gene changes at all during all of the timesteps of the gene expression series data, and (iv) how often the activation/expression state indicator of the particular gene changes during a specified timestep window of the gene expression series data. In some embodiments, once a cross-temporal gene state change frequency indicator is generated for each gene, then those activation/expression state indicators that correspond to genes whose cross-temporal gene state change frequency indicators fail to satisfy a cross-temporal gene state change frequency indicator threshold are removed from gene expression series data. In some embodiments, one objective of this operation is to reduce the input data size by removing data associated with genes having no or low activation/expression state change.

The term "gene designation" may refer to a data construct that describes one or more genes. In some embodiments, the gene designation of a gene is a designation of the gene that applies only to the gene. In some embodiments, the gene designation of a gene is a designation of the gene that applies only to the gene that are deemed sufficiently related to the gene, e.g., that are in the co-state gene cluster of the gene. Aspects of co-state gene clusters are described in greater detail below.

The term "co-state gene cluster" may refer to a data construct that is configured to describe a subset of genes that, within the gene expression series data, always have the same activation/expression state indicator within a common timestep of the gene expression series data. For example, if, for each timestep 1, the activation/expression state indicator for a first gene at timestep/is the same as the activation/expression state for a second gene at timestep/, then the two genes may be in a common co-state gene cluster. In some embodiments, once updated, the gene expression series data depicts the activation/expression state indicator for each co-state gene cluster at each timestep, instead of depicting the activation/expression state indicator for each individual gene at each timestep. This may also be intended to reduce the input data size. In some embodiments, each co-state gene cluster corresponds to a gene designation, which may in some embodiments include co-state gene clusters each including one or more genes having the same activation/expression state indicator as a particular gene within a common timestep of the gene expression series data, while in other embodiments a gene designation may simply refer to a gene.

The term "gene designation predictor set" may refer to a data construct that describes one or more gene designation predictors for the particular gene designation, where each gene designation predictor for the particular gene designation may describe that a temporally precedent value of one or more temporally precedent gene designations affects a temporally subsequent value of the particular gene designation. In some embodiments, to generate a gene designation predictor set for a particular gene designation that is associated with one or more co-clustered genes, a predictive data analysis computing entity: (i) identifies each timestep at which (according to the gene expression data) the particular gene designation has changed form an affirmative action/expression state indicator (e.g., a one-valued action/expression state indicator) to a negative action/expression state indicator (e.g., a zero-valued action/expression state indicator) or vice versa, (ii) for each identified timestep, iterates/timesteps before the identified timestep and records each combination of gene designation action/expression state indicators whose value changes during a timestep of the iterated/timesteps, and (iii) determines each recorded combination as a gene designation predictor for the particular gene designation. Accordingly, each gene designation predictor for a particular gene designation may correspond to a combination of one or more gene designations, where: (i) the action/expression state indicator of all of the gene designations in the combinations changes at a particular timestep, and (ii) the particular timestep is within/temporally precedent (i.e., previous) timesteps of a particular timestep within which the action/expression state indicator for the particular gene designation changes. In some embodiments,/ is a user-defined hyper-parameter of the predictive data analysis system 101. In some embodiments,/is determined using a temporally precedent time window machine learning model based at least in part on one or more features of the gene expression data.

The term "cross-temporal gene state transformation relationship" may refer to a data construct that describes that a temporally precedent value (e.g., temporally precedent activation/expression state indicators) of one or more first gene designations affects a temporally subsequent (i.e., later) value (e.g., temporally precedent activation/expression state indicators) of one or more second gene designations. In some embodiments, to generate cross-temporal gene state transformation for a particular gene designation that is associated with one or more co-clustered genes, a predictive data analysis computing entity: (i) identifies each timestep at which (according to the gene expression data) the particular gene designation has changed form an affirmative action/expression state indicator (e.g., a one-valued action/expression state indicator) to a negative action/expression state indicator (e.g., a zero-valued action/expression state indicator) or vice versa, (ii) for each identified timestep, iterates/timesteps before the identified timestep and records each gene designation whose gene designation action/expression state indicator changes during a timestep of the iterated/timesteps, and (iii) determines a cross-temporal gene state transformation based at least in part on each recorded gene designation in relation to the particular gene designation.

The term "transformation relationship model" may refer to a data construct that describes a relationship expressed based at least in part on the activation/expression state indicators of a set of gene designations, where the relationship is determined based at least in part on a cross-temporal gene state transformation that is associated with the gene designations. For example, when a first potential predictor set is associated with the cross-temporal gene state transformation relationship G1'=G2 and a second potential predictor set is associated with the cross-temporal gene state transformation relationship G2'=G1$\wedge$G3, the CNF model of the potential predictor sets may include the model/expression $(\neg G1 \vee G2') \wedge (\neg G2' \vee G1) \wedge (\neg G2' \vee G3)$, where $(\neg G1 \vee G2')$ is the disjunctive term corresponding to the first potential predictor set, and where $(\neg G2' \vee G1)$ and $(\neg G2' \vee G3)$ are the disjunctive terms corresponding to the second potential predictor set. In this example, each disjunctive clause of the CNF model may be deemed to be a transformation relationship model. In the preceding example, G1, G2, and G3 each correspond to a state of a first gene, a second gene, and a third gene at a current timestep (i.e., a timestep t), while G1', G2' and G3' each correspond to a state of the first gene, the second gene, and the third gene at a next timestep (i.e., a timestep t+m, where m may be 1 or another non-zero positive integer). Moreover, in the preceding example, ∧ corresponds to an AND operation while ∨ corresponds to an OR operation.

The term "potential predictor set" may refer to a data construct that describes a combination of gene designation predictors for each gene designation that is associated with a particular set of gene expression data. In some embodiments, given a set of gene designation predictor sets for a set of gene designations, each potential predictor set includes one gene designation predictor from each gene designation predictor set. Accordingly, in some embodiments, given a first gene designation predictor set for a first gene designation that includes n gene designation predictors and a second gene designation predictor set for a second gene designation that includes m gene designators, up to n*m potential predictors set may be generated, each including one gene designation predictor from the first gene designation predictor set and another gene designation predictor from the second gene designation predictor set.

The term "conjunctive predictor representation" may refer to a data construct that describes, for each potential predictor set of a set of potential predictor sets, a conjunctive predictor set representation. An example of a conjunctive predictor representation is a conjunctive normal form (CNF) model that is a conjunction of various disjunctive terms, where each disjunctive term of the CNF model corresponds to a potential predictor set, and where a disjunctive term for a potential predictor set is itself a disjunction of input terms corresponding to activation/expression state indicators of gene designations that are associated with a corresponding cross-temporal gene state transformation relationships of the potential predictor set. For example, when a first potential predictor set is associated with the cross-temporal gene state transformation relationship $G1'=G2$ and a second potential predictor set is associated with the cross-temporal gene state transformation relationship $G2'=G1 \wedge G3$, the CNF model of the potential predictor sets may include the model/expression $(\neg G1 \vee G2') \wedge (\neg G2' \vee G1) \wedge (\neg G2' \vee G3)$, where $(\neg G1 \vee G2')$ is a disjunctive term corresponding to the first potential predictor set, and where $(\neg G2' \vee G1)$ and $(\neg G2' \vee G3)$ are disjunctive terms corresponding to the second potential predictor set. In the preceding example, G1, G2, and G3 each correspond to a state of a first gene, a second gene, and a third gene at a current timestep (i.e., a timestep t), while G1', G2' and G3' each correspond to a state of the first gene, the second gene, and the third gene at a next timestep (i.e., a timestep t+m, where m may be 1 or another non-zero positive integer). Moreover, in the preceding example, ∧ corresponds to an AND operation while ∨ corresponds to an OR operation.

The term "conjunctive predictor set representation" may refer to a data construct that describes a conjunction of various disjunctive terms, where each disjunctive term is a disjunction of various input terms, and where the input terms are determined based at least in part on gene designations that are associated with a corresponding cross-temporal gene state transformation relationship of a corresponding potential predictor set. For example, if a potential predictor set describes a cross-temporal gene state transformation relationship between a first gene designation and a second gene designation, the conjunctive predictor set representation for the potential predictor set may have a disjunctive term that is associated with a disjunction of at least one input term corresponding to the first gene designation and at least one input term corresponding to the second gene designation. As another example, if a potential predictor set describes a cross-temporal gene state transformation relationship between a temporally precedent value of a first gene designation, a temporally precedent value of a second gene designation, and a temporally subsequent value of a third gene designation, then the potential predictor set may be associated with one disjunctive term that is a disjunction of input terms determined based at least in part on the first gene designation and the third gene designation, as well as another disjunctive term that is a disjunction of input terms determined based at least in part on the third gene designation and the third gene designation.

The term "eligibility indicator" may refer to a data construct that describes whether a particular potential predictor set should be part of an optimal predictor set. In some embodiments, to generate the eligibility indicator for a potential predictor set, the predictive data analysis computing entity 106 generates a quantum processing unit for the potential predictor set that comprises, for each transformation relationship model of the potential predictor set: (i) a plurality of gene designation superposition qubits for a plurality of affected qubits of the cross-temporal gene transformation relationship that is associated with the transformation relationship model, and (ii) an ancilla qubit whose value is determined based at least in part on the plurality of gene designation superposition qubits. In some of the noted embodiments, after generating the quantum processing units for the potential predictor sets, a quantum logic circuit is generated that (i) comprises one or more quantum logic subcircuits for each quantum processing unit, and (ii) is configured to perform a conjunctive phase logic operation on each ancilla bit. In some embodiments, the eligibility indicator is generated based at least in part the output of the conjunctive phase logic operation.

The term "optimal predictor set" may refer to a data construct that is configured to describe a set of satisfiable potential predictor sets for a gene regulatory network. In some embodiments, the optimal predictor set describes each steady state of the gene regulatory network, such as states in which gene regulatory network states have a cyclical behavior.

III. Computer Program Products, Methods, and Computing Entities

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query, or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established, or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations. Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically configured machines performing the steps or operations specified in the block diagrams and flowchart illustrations. Accordingly, the block diagrams and flowchart illustrations support various combinations of embodiments for performing the specified instructions, operations, or steps.

IV. Exemplary System Architecture

FIG. 1 is a schematic diagram of an example architecture 100 for performing health-related predictive data analysis. The architecture 100 includes a predictive data analysis system 101 configured to receive health-related predictive data analysis requests from external computing entities 102, process the predictive data analysis requests to generate health-related risk predictions, provide the generated health-related risk predictions to the external computing entities 102, and automatically perform prediction-based actions based at least in part on the generated polygenic risk score predictions. Examples of health-related predictions include genetic risk predictions, polygenic risk predictions, medical risk predictions, clinical risk predictions, behavioral risk predictions, and/or the like.

In some embodiments, predictive data analysis system 101 may communicate with at least one of the external computing entities 102 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The predictive data analysis system 101 may include a predictive data analysis computing entity 106 and a storage subsystem 108. The predictive data analysis computing entity 106 may be configured to receive health-related predictive data analysis requests from one or more external computing entities 102, process the predictive data analysis requests to generate the polygenic risk score predictions corresponding to the predictive data analysis requests, provide the generated polygenic risk score predictions to the external computing entities 102, and automatically perform prediction-based actions based at least in part on the generated polygenic risk score predictions.

The storage subsystem 108 may be configured to store input data used by the predictive data analysis computing entity 106 to perform health-related predictive data analysis as well as model definition data used by the predictive data analysis computing entity 106 to perform various health-related predictive data analysis tasks. The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Predictive Data Analysis Computing Entity

FIG. 2 provides a schematic of a predictive data analysis computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the predictive data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the predictive data analysis computing entity 106 may include or be in communication with one or more processing elements 205 (also referred to as processors, processing circuitry, and/or similar terms used herein interchangeably) that communicate with other elements within the predictive data analysis computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the predictive data analysis computing entity 106 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the predictive data analysis computing entity 106 may further include or be in communication with volatile media (also referred to as volatile storage, memory, memory storage, memory circuitry and/or similar terms used herein interchangeably). In one embodiment, the volatile storage or memory may also include one or more volatile storage or memory media 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the predictive data analysis computing entity 106 with the assistance of the processing element 205 and operating system.

As indicated, in one embodiment, the predictive data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the predictive data analysis computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the predictive data analysis computing entity 106 may include or be in communication with one or more input elements, such as a keyboard input, a mouse input, a touch screen/display input, motion input, movement input, audio input, pointing device input, joystick input, keypad input, and/or the like. The predictive data analysis computing entity 106 may also include or be in communication with one or more output elements (not shown), such as audio output, video output, screen/display output, motion output, movement output, and/or the like.

Exemplary External Computing Entity

FIG. 3 provides an illustrative schematic representative of an external computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. External computing entities 102 can be operated by various parties. As shown in FIG. 3, the external computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the external computing entity 102 may be capable of operating with one or more air interface standards, communication protocols, modulation types, and access types. More particularly, the external computing entity 102 may operate in accordance with any of a number of wireless communication standards and protocols, such as those described above with regard to the predictive data analysis computing entity 106. In a particular embodiment, the external computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the external computing entity 102 may operate in accordance with multiple wired communication standards and protocols, such as those described above with regard to the predictive data analysis computing entity 106 via a network interface 320.

Via these communication standards and protocols, the external computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The external computing entity 102 can also download changes, add-ons, and updates, for instance, to its firmware, software (e.g., including executable instructions, applications, program modules), and operating system.

According to one embodiment, the external computing entity 102 may include location determining aspects, devices, modules, functionalities, and/or similar words used herein interchangeably. For example, the external computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the external computing entity's 102 position in connection with a variety of other systems, including cellular towers, Wi-Fi access points, and/or the like. Similarly, the external computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The external computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the external computing entity 102 to interact with and/or cause display of information/data from the predictive data analysis computing entity 106, as described herein. The user input interface can comprise any of a number of devices or interfaces allowing the external computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the external computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The external computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the external computing entity 102. As indicated, this may include a user application that is resident on the entity or accessible through a browser or other user interface for communicating with the predictive data analysis computing entity 106 and/or various other computing entities.

In another embodiment, the external computing entity 102 may include one or more components or functionality that are the same or similar to those of the predictive data analysis computing entity 106, as described in greater detail above. As will be recognized, these architectures and descriptions are provided for exemplary purposes only and are not limiting to the various embodiments.

In various embodiments, the external computing entity 102 may be embodied as an artificial intelligence (AI) computing entity, such as an Amazon Echo, Amazon Echo Dot, Amazon Show, Google Home, and/or the like. Accordingly, the external computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

V. Exemplary System Operations

As described below, various embodiments of the present invention address the above-noted challenges associated with computational complexity of generating gene regulatory networks from gene expression data by utilizing quantum computing techniques. For example, some embodiments comprise generating an optimal predictor set for a gene regulatory network using a quantum logic circuit that comprises one or more quantum logic subcircuits for each quantum processing unit that is associated with a quantum subcircuit and is configured to perform a conjunctive phase logic operation performed on each ancilla bit of a quantum subcircuit. By using the noted techniques, various embodiments of the present invention address the technical challenges associated with generating gene regulatory networks from gene expression data in a computationally efficient manner and make important contributions to the field of computational genomics. Moreover, various embodiments of the present invention use quantum computing to determine the predictor set of a gene regulatory network, which is the set of genes of a gene regulatory network whose state at a time/affects the state of the gene regulatory network at a time t+1.

FIG. 4 is a flowchart diagram of an example process 400 for determining an optimal predictor set based at least in part on a particular set of gene expression data. Via the various steps/operations of the process 400, the predictive data analysis computing entity 106 can perform scalable and computationally efficient gene predictor set computation by using quantum computing techniques described herein.

The process 400 begins at step/operation 401 when the predictive data analysis computing entity 106 identifies (e.g., receives) the gene expression data (e.g., including gene expression data describing single-cell RNA-seq data for GRN analysis (scRNA)). The gene expression data may describe, for each gene of a plurality of observed genes of a monitored individual, a recorded expression value at each of a plurality of timesteps. For example, the gene expression data may describe that a first gene is expressed with a first expression value at time $t_1$, a second expression value at time $t_2$, and so on, while a second gene is expressed with a third expression value at a time $t_3$, a fourth expression value at time $t_4$, and so on.

An operational example of gene expression data 500 is depicted in FIG. 5. As depicted in FIG. 5, each row of the depicted table corresponds to a particular gene and a particular timestep. For example, the first row of the depicted table depicts that a particular gene that is associated with the first row is expressed at a timestep that is associated with the first row with an expression value of 111.824. As another example, the second row of the depicted table depicts that a particular gene that is associated with the second row is expressed at a timestep that is associated with the second row with an expression value of 126.907. As yet another example, the third row of the depicted table depicts that a particular gene is associated with the third row is expressed at a timestep that is associated with the third row with an expression value of 92.20126.

At step/operation 402, the predictive data analysis computing entity 106 generates gene expression series data based at least in part on the gene expression data. The gene expression series data may describe, for each timestep of a plurality of timesteps, which genes are activated/expressed at the particular timestep via an activation/expression state indicator for each gene at a particular timestep. For example, the gene expression series data may describe that, at a time $t_1$, a first gene is activated/expressed while a second gene is not activated/expressed. In some embodiments, to determine whether a particular gene is activated/expressed at a particular timestep, the expression value for the particular gene and the particular timestep may be extracted from the gene series data. If the expression value for the particular gene and the particular timestep satisfies (e.g., exceeds) a threshold expression value, then the gene expression series data may describe that the particular gene is activated/expressed at the particular timestep.

An operational example of gene expression series data 600 is depicted in FIG. 6. As depicted in FIG. 6, at time $t_1$, gene expression series data 600 describes that gene 1 is not activated/expressed, gene 2 is activated/expressed, and gene 3 is not activated/expressed. As further depicted in FIG. 6, at time $t_2$, gene expression series data 600 describes that gene 1 is activated/expressed, gene 2 is not activated/expressed, and gene 3 is not activated/expressed.

At step/operation 403, the predictive data analysis computing entity 106 optionally updates the gene expression series data by performing at least one of the following operations: (i) removing from the gene expression data all activation/expression state indicators for a non-qualified subset of genes that are not associated with a threshold-satisfying cross-temporal gene state change frequency indicator, and (ii) replacing each activation/expression state indicator for a gene with an activation/expression state indicator for a co-state gene cluster of the gene.

In some embodiments, a cross-temporal gene state change frequency indicator is a measure of how frequently the activation/expression state indicator of a corresponding gene changes across the various timesteps described by the gene expression series data. For example, the cross-temporal gene state change frequency indicator for a particular gene may be determined based at least in part on at least one of: (i) whether the activation/expression state indicator of the particular gene changes at all during all of the timesteps of the gene expression series data, (ii) whether the activation/expression state indicator of the particular gene changes at least once during each defined-size timestep window of the gene expression series data, (iii) how often the activation/expression state indicator of the particular gene changes at all during all of the timesteps of the gene expression series data, and (iv) how often the activation/expression state indicator of the particular gene changes during a specified timestep window of the gene expression series data.

In some embodiments, once a cross-temporal gene state change frequency indicator is generated for each gene, then those activation/expression state indicators that correspond to genes whose cross-temporal gene state change frequency indicators fail to satisfy a cross-temporal gene state change frequency indicator threshold are removed from gene expression series data. In some embodiments, one objective of this operation is to reduce the input data size by removing data associated with genes having no or low activation/expression state change.

In some embodiments, the co-state gene cluster describes a subset of genes that, within the gene expression series data, always have the same activation/expression state indicator within a common timestep of the gene expression series data. For example, if, for each timestep t, the activation/expression state indicator for a first gene at timestep t is the same as the activation/expression state for a second gene at timestep t, then the two genes may be in a common co-state gene cluster. In some embodiments, once updated, the gene expression series data depicts the activation/expression state indicator for each co-state gene cluster at each timestep, instead of depicting the activation/expression state indicator for each individual gene at each timestep. This may also be intended to reduce the input data size. In some embodiments, each co-state gene cluster corresponds to a gene designation, which may in some embodiments include co-state gene clusters each including one or more genes having the same activation/expression state indicator as a particular gene within a common timestep of the gene expression series data, while in other embodiments a gene designation may simply refer to a gene.

At step/operation 404, the predictive data analysis computing entity 106 generates a gene designation predictor set for each gene designation described by the gene designation series data, where the gene designation predictor set for a particular gene designation describes one or more gene designation predictors for the particular gene designation, and where each gene designation predictor for the particular gene designation describes that a temporally precedent value of one or more temporally precedent gene designations affects a temporally subsequent value of the particular gene designation. In some embodiments, to generate a gene designation predictor set for a particular gene designation that is associated with one or more co-clustered genes, the predictive data analysis computing entity 106: (i) identifies each timestep at which (according to the gene expression data) the particular gene designation has changed form an affirmative action/expression state indicator (e.g., a one-valued action/expression state indicator) to a negative action/expression state indicator (e.g., a zero-valued action/expression state indicator) or vice versa, (ii) for each identified timestep, iterates t timesteps before the identified timestep and records each combination of gene designation action/expression state indicators whose value changes during a timestep of the iterated t timesteps, and (iii) determines each recorded combination as a gene designation predictor for the particular gene designation. Accordingly, each gene designation predictor for a particular gene designation may correspond to a combination of one or more gene designations, where: (i) the action/expression state indicator of all of the gene designations in the combinations changes at a particular timestep, and (ii) the particular timestep is within t temporally precedent (i.e., previous) timesteps of a particular timestep within which the action/expression state indicator for the particular gene designation changes. In some embodiments, t is a user-defined hyper-parameter of the predictive data analysis system 101. In some embodiments, t is determined using a temporally precedent time window machine learning model based at least in part on one or more features of the gene expression data.

At step/operation 405, the predictive data analysis computing entity 106 generates a plurality of potential predictor sets based at least in part on each gene designation predictor set for a particular gene designation of the plurality of gene designations. In some embodiments, a potential predictor set describes one or more cross-temporal gene state transformation relationships, where a cross-temporal gene state transformation describes that a temporally precedent value of one or more first gene designations affects a temporally subsequent (i.e., later) value of one or more second gene designations.

In some embodiments, a potential predictor set is a combination of gene designation predictors for each gene designation that is associated with a particular set of gene expression data. In some embodiments, given a set of gene designation predictor sets for a set of gene designations, each potential predictor set includes one gene designation predictor from each gene designation predictor set. Accordingly, in some embodiments, given a first gene designation predictor set for a first gene designation that includes n gene designation predictors and a second gene designation predictor set for a second gene designation that includes m gene designators, up to n*m potential predictors set may be generated, each including one gene designation predictor from the first gene designation predictor set and another gene designation predictor from the second gene designation predictor set.

An operational example of generating a potential predictor set is depicted in FIG. 7. As depicted in FIG. 7, given three gene designations 701-703, three corresponding gene designation predictors sets 711-713 are generated. As further depicted in FIG. 7, the potential predictor set 721 is generated based at least in part on one gene designation predictor from each of the three gene designation predictors sets 711-713.

As described above, each potential predictor set is associated with a set of cross-temporal gene state transformation relationships, where a cross-temporal gene state transformation relationship describes that a temporally precedent value of one or more first gene designations affects a temporally subsequent (i.e., later) value of one or more second gene designations. For example, the following cross-temporal gene state transformation relationships may be determined based at least in part on exemplary gene expression data that is associated with two timesteps only: (i) G1'=G2, (ii) G2'=G1$\wedge$G3, and (iii) G3'=–G1. In this example, the first cross-temporal gene state transformation relationship describes that a temporally precedent value of the activation/expression state indicator of the gene designation G2 affects a temporally subsequent value of the activation/expression state indicator of the gene designation G1, the second cross-temporal gene state transformation relationship describes that an output of a Boolean AND operation performed on the temporally precedent value of the activation/expression state indicator of the gene designation G1 and the temporally precedent value of the activation/expression state indicator of the gene designation G3 affects a temporally subsequent value of the activation/expression state indicator of the gene designation G2, and the third cross-temporal gene state transformation relationship describes that an output of a Boolean negation operation performed on the temporally precedent value of the activation/expression state indicator of the gene designation G1 affects a temporally subsequent value of the activation/expression state indicator of the gene designation G2. In some embodiments, the noted three cross-temporal gene state transformation relationships may be determined based at least in part on the gene expression state transition data that is depicted in FIG. 12.

At step/operation 406, the predictive data analysis computing entity 106 generates a conjunctive predictor representation that describes, for each potential predictor set of a set of potential predictor sets, a conjunctive predictor set representation. An example of a conjunctive predictor representation is a conjunctive normal form (CNF) model that is a conjunction of various disjunctive terms, where each disjunctive term of the CNF model corresponds to a potential predictor set, and where a disjunctive term for a potential predictor set is itself a disjunction of input terms corresponding to activation/expression state indicators of gene designations that are associated with a corresponding cross-temporal gene state transformation relationships of the potential predictor set. For example, when a first potential predictor set is associated with the cross-temporal gene state transformation relationship G1'=G2 and a second potential predictor set is associated with the cross-temporal gene state transformation relationship G2'=G1$\wedge$G3, the CNF model of the potential predictor sets may include the model/expression $(\neg G1 \vee G2') \wedge (\neg G2' \vee G1) \wedge (\neg G2' \vee G3)$, where $(\neg G1 \vee G2')$ is a disjunctive term corresponding to the first potential predictor set, and where $(\neg G2' \vee G1)$ and $(\neg G2' \vee G3)$ are disjunctive terms corresponding to the second potential predictor set.

In some embodiments, a conjunctive predictor set representation is a conjunction of various disjunctive terms, where each disjunctive term is a disjunction of various input terms, and where the input terms are determined based at least in part on gene designations that are associated with a corresponding cross-temporal gene state transformation relationship of a corresponding potential predictor set. For example, if a potential predictor set describes a cross-temporal gene state transformation relationship between a first gene designation and a second gene designation, the conjunctive predictor set representation for the potential predictor set may have a disjunctive term that is associated with a disjunction of at least one input term corresponding to the first gene designation and at least one input term corresponding to the second gene designation. As another example, if a potential predictor set describes a cross-temporal gene state transformation relationship between a temporally precedent value of a first gene designation, a temporally precedent value of a second gene designation, and a temporally subsequent value of a third gene designation, then the potential predictor set may be associated with one disjunctive term that is a disjunction of input terms determined based at least in part on the first gene designation and the third gene designation, as well as another disjunctive term that is a disjunction of input terms determined based at least in part on the third gene designation and the third gene designation.

In some embodiments, to generate a CNF model based at least in part on a set of potential predictor sets, the predictive data analysis computing entity 106 uses a REVEAL algorithm to infer node interactions from measures of mutual information from state transition tables. Aspects of the REVAL algorithm are described in Keleman et al., Computational Intelligence in Bioinformatics (2008). In some embodiments, to generate a CNF model based at least in part on a set of potential predictor sets, for each designations, a set of all active gene designations in a previous state of the gene designation and another set of all passive gene designations in a previous state of the gene designation are combined.

At step/operation 407, the predictive data analysis computing entity 106 performs one or more quantum computing operations to determine an optimal predictor set based at least in part on the conjunctive predictor set representations of the potential predictor sets. In some embodiments, the quantum computing operations are configured to generate an eligibility indicator for each potential predictor set that describes whether a particular potential predictor set should be part of an optimal predictor set. In some embodiments, to generate the eligibility indicator for a potential predictor set, the predictive data analysis computing entity 106 generates a quantum processing unit for the potential predictor set that comprises, for each transformation relationship model of the potential predictor set: (i) a plurality of gene designation superposition qubits for a plurality of affected qubits of the cross-temporal gene transformation relationship that is associated with the transformation relationship model, and (ii) an ancilla qubit whose value is determined based at least in part on the plurality of gene designation superposition qubits. In some of the noted embodiments, after generating the quantum processing units for the potential predictor sets, a quantum logic circuit is generated that (i) comprises one or more quantum logic subcircuits for each quantum processing unit, and (ii) is configured to perform a conjunctive phase logic operation on each ancilla bit. In some embodiments, the eligibility indicator is generated based at least in part on the output of the conjunctive phase logic operation.

In some embodiments, an optimal predictor set describe a set of satisfiable potential predictor sets for a gene regulatory network. In some embodiments, the optimal predictor set describes each steady state of the gene regulatory network, such as states in which gene regulatory network states have a cyclical behavior. For example, for the gene regulatory network corresponding to FIG. 7, the two steady/attractor states depicted in FIG. 10 may be described by the optimal predictor set for the gene regulatory network.

In some embodiments, step/operation 407 may be performed in accordance with the process that is depicted in FIG. 8. The process that is depicted in FIG. 8 begins at step/operation 801 when the predictive data analysis computing entity 106 generates, for each transformation relationship model of a potential predictor set, a quantum processing unit. The quantum processing unit for a transformation relationship model may include gene designation superposition qubits which are qubits that correspond to inputs terms of the conjunctive predictor set representation for the transformation relationship model, where the values of the noted qubits may be defined based at least in part on activation/expression state indicators of gene designations that are associated with the disjunctive operation of the transformation relationship model. The quantum processing unit for a potential predictor set may also include an ancilla qubit whose value is determined based at least in part on the output of the disjunctive operations performed on the input terms.

An operational example of a quantum processing unit 900 is depicted in FIG. 9. As depicted in FIG. 9, the quantum processing unit 900 includes the gene designation superposition qubits 901-903 corresponding to three input terms that are determined based at least in part on superposition of activation/expression state indicators for gene designations G1, G2', and G3. As further depicted in FIG. 9, the quantum processing unit 900 further includes the ancilla qubit 904 that represents the superposition of the output corresponding to the disjunction of the three input terms. The superpositions for the gene designation superposition qubits 901-903 and/or the ancilla qubit 904 may be imposed using Hadamard gates, such as Hadamard gates that impose a 50% chance of being ON for each of the gene designation superposition qubits 901-903, and/or Hadamard gates that impose a 75% chance of being ON for the ancilla qubit 904 that represents the superposition of the output corresponding to the disjunction of the three input terms.

As described above, each potential predictor set may be associated with at least one disjunctive sub-model/clause of a CNF model/expression. Accordingly, in some embodiments, each disjunctive sub-model/clause of a CNF model/expression may be mapped to a separate quantum processing unit. In some embodiments, prior to measurement operations involving a conjunctive phase logic operation, each of the ancilla qubits represent an intermediate output of each disjunctive sub-model/clause in a superposition state.

At step/operation 802, the predictive data analysis computing entity 106 generates a quantum logic circuit that: (i) comprises one or more quantum logic subcircuits for each quantum processing unit, and (ii) is configured to perform a conjunctive phase logic operation on each ancilla bit. In some embodiments, the predictive data analysis computing entity 106 encodes each quantum processing unit into a quantum logic subcircuit and then generates a quantum logic circuit that performs a conjunctive phase logic operation on each ancilla bit of a quantum logic subcircuit.

At step/operation 803, the predictive data analysis computing entity 106 stores output superposition states of each quantum logic subcircuit in the ancilla qubit of the quantum logic subcircuit. In some embodiments, the ancilla qubit of the quantum logic subcircuit is out of the superposition state after step/operation 803 and has a measurement that corresponds to an observed output of the disjunction operations of the input terms corresponding to the quantum processing unit that is associated with the quantum logic subcircuit.

At step/operation 804, the predictive data analysis computing entity 106 performs a conjunctive phase flip operation (e.g., a phase flip AND operation) on each ancilla qubit of a quantum logic subcircuit to generate an observed value for quantum logic circuit. In some embodiments, a phase flip AND operation is performed using the output stored on ancilla qubits of quantum logic subcircuits to generate the observed value for quantum logic circuit.

At step/operation 805, the predictive data analysis computing entity 106 generates an equivalent decoder subcircuit for each potential predictor set to maintain the reversibility requirement for the quantum operations of the quantum logic subcircuit for the potential predictor set. In some embodiments, the equivalent decoder subcircuit for a potential predictor set converts the ancilla bit of the quantum logic subcircuit of the potential predictor set to the input terms of the disjunction operation of the quantum logic subcircuit of the potential predictor set.

At step/operation 806, the predictive data analysis computing entity 106 performs a Grover mirror iteration on the quantum processing unit comprising the quantum logic circuit and the equivalent decoder subcircuits for the potential predictor sets that are associated with the quantum logic circuit to generate the hidden phase data for each potential predictor set. In some embodiments, generating the eligibility indicator for a particular potential predictor set comprises performing a Grover mirror operation based at least in part on the quantum logic subcircuit for the potential predictor set to generate hidden phase data for the particular potential predictor set; and generating the eligibility indicator for the particular potential predictor set based at least in part on the hidden phase data for the particular potential predictor set. In some embodiments, generating the eligibility indicator for a particular potential predictor set comprises performing a Grover mirror operation based at least in part on the quantum logic subcircuit for the potential predictor set and using the equivalent decoder subcircuit for the quantum logic subcircuit to generate hidden phase data for the particular potential predictor set; and generating the eligibility indicator for the particular potential predictor set based at least in part on the hidden phase data for the particular potential predictor set.

In some embodiments, a Grover mirror operation comprises one or more Grover mirror iterations, where the number of Grover iterations may be determined based at least in part on a predictive output (e.g., the predictive output of a machine learning model that is trained based at least in part on historical success scenarios for similar problems), based at least in part on user preferences defined in a configuration file, and/or based at least in part on the output of the equation $$N_{grover} = \frac{\pi}{4}\sqrt{2^n},$$

where n may be the number of qubits (i.e., gene designation qubits and the ancilla qubits) on which the Grover mirror iteration of the Grover mirror operation is performed. In some embodiments, the Grover mirror operations comprises one or more Grover mirror iterations each associated with an amplitude amplification iteration count, and each amplitude amplification iteration count for a particular Grover mirror iteration is determined based at least in part on historical execution data for the particular Grover mirror iteration.

At step/operation 807, the predictive data analysis computing entity 106 determines whether more Grover mirror iterations are outstanding (i.e., required to be performed but not already performed). Afterward, in response to determining that more Grover mirror iterations are outstanding, the predictive data analysis computing entity 106 proceeds to perform those Grover mirror iterations; otherwise, at step/operation 808, based at least in part on the hidden phase data for each potential predictor set, the eligibility indicator for the potential predictor set is determined and the optimal predictor set is determined based at least in part on each potential predictor set having an affirmative eligibility indicator.

In some embodiments, to perform quantum computing operations described above, a suitable quantum computer having a required number of qubits, a required number of number or ancillary qubits, a required de-coherence time, and/or a required gate fidelity is selected. In some embodiments, the hardware of the selected quantum computer is optimized for the quantum logic circuit described above. After performing the quantum operations, a measurement operation may be performed to the output quantum states from the quantum registers to the classical registers. The eligibility indicators may be determined based at least in part on satisfying cubes (e.g., conjunction of literals) detected by the quantum computer each encoding a potential predictor set for a given gene regulatory network (GRN).

In some embodiments, after generating the optimal predictor set, the predictive data analysis computing entity 106 generates a genetic risk score based at least in part on the optimal predictor set and performs prediction-based actions based at least in part on the genetic risk. Examples of prediction-based actions including displaying a user interface that displays health-related risk predictions (e.g., at least one of epistatic polygenic risk scores, epistatic interaction scores, and base polygenic risk scores) for a target individual with respect to a set of conditions. For example, as depicted in FIG. 11, the predictive output user interface 1100 depicts the health-related risk prediction for a target individual with respect to four target conditions each identified by the International Statistical Classification of Diseases and Related Health Problems (ICD) code of the noted four target conditions.

Accordingly, various embodiments of the present invention address the above-noted challenges associated with computational complexity of generating gene regulatory networks from gene expression data by utilizing quantum computing techniques. For example, some embodiments comprise generating an optimal predictor set for a gene regulatory network using a quantum logic circuit that comprises one or more quantum logic subcircuits for each quantum processing unit that is associated with a quantum subcircuit and is configured to perform a conjunctive phase logic operation performed on each ancilla bit of a quantum subcircuit. By using the noted techniques, various embodiments of the present invention address the technical challenges associated with generating gene regulatory networks from gene expression data in a computationally efficient manner and make important contributions to the field of computational genomics.

VI. Conclusion

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method comprising:
identifying, by one or more processors and based at least in part on gene expression data for a plurality of genes, a plurality of potential predictor sets for a target gene designation, wherein a potential predictor set of the plurality of potential predictor sets is associated with one or more cross-temporal gene state transformation relationships;
generating, by the one or more processors, a conjunctive predictor set representation for the potential predictor set, wherein the conjunctive predictor set representation describes a conjunction of one or more transformation relationship models associated with the one or more cross-temporal gene state transformation relationships;
generating, by the one or more processors, at least one quantum processing unit that comprises: (i) at least one gene designation superposition qubit for a plurality of affected qubits of the one or more cross-temporal gene state transformation relationships, wherein the at least one gene designation superposition qubit is associated with at least one of the one or more transformation relationship models, and (ii) an ancilla qubit whose value is determined based at least in part on the at least one gene designation superposition qubit;
generating, by the one or more processors, a quantum logic circuit that (i) comprises one or more quantum logic subcircuits for the at least one quantum processing unit, and (ii) is configured to perform a conjunctive phase logic operation on the ancilla qubit;

generating, by the one or more processors, an eligibility indicator for the potential predictor set based at least in part on an output of the conjunctive phase logic operation;

determining, by the one or more processors, an optimal predictor set based at least in part on the potential predictor set having an affirmative eligibility indicator;

determining, by the one or more processors, a genetic risk score based at least in part on the optimal predictor set; and causing, by the one or more processors and via a user interface, display of a health-related risk prediction associated with the genetic risk score for a target individual, wherein the target individual meets a set of conditions associated with the genetic risk score.

2. The computer-implemented method of claim 1, wherein generating the eligibility indicator for the potential predictor set comprises:

performing a Grover mirror operation based at least in part on the one or more quantum logic subcircuits for the potential predictor set to generate hidden phase data for the potential predictor set; and generating the eligibility indicator for the potential predictor set based at least in part on the hidden phase data for the potential predictor set.

3. The computer-implemented method of claim 2, wherein:

the Grover mirror operation comprises one or more Grover mirror iterations each associated with an amplitude amplification iteration count, and the amplitude amplification iteration count for each particular Grover mirror iteration of the one or more Grover mirror iterations is determined based at least in part on historical execution data for the particular Grover mirror iteration.

4. The computer-implemented method of claim 1, wherein the one or more quantum logic subcircuits further comprise an equivalent decoder subcircuit.

5. The computer-implemented method of claim 1, wherein each transformation relationship model of the one or more transformation relationship models is a disjunctive representation of a cross-temporal gene state transformation relationship that is associated with the transformation relationship model.

6. The computer-implemented method of claim 1, wherein identifying the plurality of potential predictor sets comprises:

identifying a gene designation associated with a designated subset of the plurality of genes;

determining a gene designation predictor set, wherein: (i) the gene designation predictor set describes one or more gene designation predictors for the gene designation, and (ii) the gene designation predictor set for the gene designation describes that a temporally precedent value of a temporally precedent gene designation affects a temporally subsequent value of the gene designation; and identifying the plurality of potential predictor sets based at least in part on the gene designation predictor set.

7. The computer-implemented method of claim 6, wherein identifying the plurality of potential predictor sets based at least in part on the gene designation predictor set comprises:

determining a gene designation predictor combination, wherein the gene designation predictor combination comprises gene designation predictors from one or more gene designation predictor sets; and identifying the plurality of potential predictor sets based at least in part on the gene designation predictor combination.

8. The computer-implemented method of claim 6, wherein identifying the plurality of potential predictor sets comprises:

determining: (i) a cross-temporal gene state change frequency indicator across the gene expression data, and (ii) a co-state gene cluster of a qualified subset of the plurality of genes having an affirmative cross-temporal gene state change frequency indicator; and identifying the plurality of potential predictor sets based at least in part on the co-state gene cluster.

9. A system comprising one or more processors and at least one memory storing processor executable instructions that, when executed by the one or more processors, cause the one or more processors to:

identify, based at least in part on gene expression data for a plurality of genes, a plurality of potential predictor sets for a target gene designation, wherein a potential predictor set of the plurality of potential predictor sets is associated with one or more cross-temporal gene state transformation relationships;

generate a conjunctive predictor set representation for the potential predictor set, wherein the conjunctive predictor set representation describes a conjunction of one or more transformation relationship models associated with the one or more cross-temporal gene state transformation relationships;

generate at least one quantum processing unit that comprises: (i) at least one gene designation superposition qubit for a plurality of affected qubits of the one or more cross-temporal gene state transformation relationships, wherein the at least one gene designation superposition qubit is associated with at least one of the one or more transformation relationship models, and (ii) an ancilla qubit whose value is determined based at least in part on the at least one gene designation superposition qubit;

generate a quantum logic circuit that (i) comprises one or more quantum logic subcircuits for the at least one quantum processing unit, and (ii) is configured to perform a conjunctive phase logic operation on the ancilla qubit;

generate an eligibility indicator for the potential predictor set based at least in part on an output of the conjunctive phase logic operation;

determine an optimal predictor set based at least in part on the potential predictor set having an affirmative eligibility indicator;

determine a genetic risk score based at least in part on the optimal predictor set; and cause, via a user interface, display of a health-related risk prediction associated with the genetic risk score for a target individual, wherein the target individual meets a set of conditions associated with the genetic risk score.

10. The system of claim 9, wherein, to generate the eligibility indicator for the potential predictor set, the at least one memory stores processor executable instructions that, when executed by the one or more processors, further cause the one or more processors to:

perform a Grover mirror operation based at least in part on the one or more quantum logic subcircuits for the potential predictor set to generate hidden phase data for the potential predictor set; and generate the eligibility indicator for the potential predictor set based at least in part on the hidden phase data for the potential predictor set.

11. The system of claim 10, wherein:
the Grover mirror operation comprises one or more Grover mirror iterations each associated with an amplitude amplification iteration count, and
the amplitude amplification iteration count for each particular Grover mirror iteration of the one or more Grover mirror iterations is determined based at least in part on historical execution data for the particular Grover mirror iteration.

12. The system of claim 9, wherein the one or more quantum logic subcircuits further comprise an equivalent decoder subcircuit.

13. The system of claim 9, wherein each transformation relationship model of the one or more transformation relationship models is a disjunctive representation of a cross-temporal gene state transformation relationship that is associated with the transformation relationship model.

14. The system of claim 9, wherein, to identify the plurality of potential predictor sets, the at least one memory stores processor executable instructions that, when executed by the one or more processors, further cause the one or more processors to:
identify a gene designation associated with a designated subset of the plurality of genes;
determine a gene designation predictor set, wherein: (i) the gene designation predictor set describes one or more gene designation predictors for the gene designation, and (ii) the gene designation predictor set for the gene designation describes that a temporally precedent value of a temporally precedent gene designation affects a temporally subsequent value of the gene designation; and
identify the plurality of potential predictor sets based at least in part on the gene designation predictor set.

15. The system of claim 14, wherein, to identify the plurality of potential predictor sets based at least in part on the gene designation predictor set, the at least one memory stores processor executable instructions that, when executed by the one or more processors, further cause the one or more processors to:
determine a gene designation predictor combination, wherein the gene designation predictor combination comprises gene designation predictors from one or more gene designation predictor sets; and
identify the plurality of potential predictor sets based at least in part on the gene designation predictor combination.

16. The system of claim 14, wherein, to identify the plurality of potential predictor sets, the at least one memory stores processor executable instructions that, when executed by the one or more processors, further cause the one or more processors to:
determine: (i) a cross-temporal gene state change frequency indicator across the gene expression data, and (ii) a co-state gene cluster of a qualified subset of the plurality of genes having an affirmative cross-temporal gene state change frequency indicator; and
identify the plurality of potential predictor sets based at least in part on the co-state gene cluster.

17. One or more non-transitory computer-readable storage media including instructions that, when executed by one or more processors, cause the one or more processors to:
identify, based at least in part on gene expression data for a plurality of genes, a plurality of potential predictor sets for a target gene designation, wherein a potential predictor set of the plurality of potential predictor sets is associated with one or more cross-temporal gene state transformation relationships;
generate a conjunctive predictor set representation for the potential predictor set, wherein the conjunctive predictor set representation describes a conjunction of one or more transformation relationship models associated with the one or more cross-temporal gene state transformation relationships;
generate at least one quantum processing unit that comprises: (i) at least one gene designation superposition qubit for a plurality of affected qubits of the one or more cross-temporal gene state transformation relationships, wherein the at least one gene designation superposition qubit is associated with at least one of the one or more transformation relationship models, and (ii) an ancilla qubit whose value is determined based at least in part on the at least one gene designation superposition qubit;
generate a quantum logic circuit that (i) comprises one or more quantum logic subcircuits for the at least one quantum processing unit, and (ii) is configured to perform a conjunctive phase logic operation on the ancilla qubit;
generate an eligibility indicator for the potential predictor set based at least in part on an output of the conjunctive phase logic operation;
determine an optimal predictor set based at least in part on the potential predictor set having an affirmative eligibility indicator;
determine a genetic risk score based at least in part on the optimal predictor set; and
cause, via a user interface, display of a health-related risk prediction associated with the genetic risk score for a target individual, wherein the target individual meets a set of conditions associated with the genetic risk score.

18. The one or more non-transitory computer-readable storage media of claim 17, wherein the instructions that cause the one or more processors to generate the eligibility indicator for the potential predictor set further cause the one or more processors to:
perform a Grover mirror operation based at least in part on the one or more quantum logic subcircuits for the potential predictor set to generate hidden phase data for the potential predictor set; and
generate the eligibility indicator for the potential predictor set based at least in part on the hidden phase data for the potential predictor set.

19. The one or more non-transitory computer-readable storage media of claim 18, wherein:
the Grover mirror operation comprises one or more Grover mirror iterations each associated with an amplitude amplification iteration count, and
the amplitude amplification iteration count for each particular Grover mirror iteration of the one or more Grover mirror iterations is determined based at least in part on historical execution data for the particular Grover mirror iteration.

20. The one or more non-transitory computer-readable storage media of claim 17, wherein the one or more quantum logic subcircuits further comprise an equivalent decoder subcircuit.

* * * * *